(12) United States Patent
Ko

(10) Patent No.: US 7,198,800 B1
(45) Date of Patent: Apr. 3, 2007

(54) COMPOSITIONS AND METHODS

(75) Inventor: Thomas Sai Ying Ko, 4 Licence Road, Belgrave South, Victoria, 3160 (AU)

(73) Assignee: Thomas Sai Ying Ko, Beijing (CN)

( * ) Notice: Subject to any disclaimer, the term of this patent is extended or adjusted under 35 U.S.C. 154(b) by 781 days.

(21) Appl. No.: 09/717,088

(22) Filed: Nov. 22, 2000

(30) Foreign Application Priority Data

Nov. 23, 1999 (AU) .................................... PQ4190

(51) Int. Cl.
*A61F 13/00* (2006.01)
*A01N 55/00* (2006.01)

(52) U.S. Cl. ...................... 424/443; 424/447; 424/448; 424/449; 424/78.35; 525/363; 514/887; 514/494; 602/43; 602/47

(58) Field of Classification Search ................ 424/443, 424/447, 448, 449, 78.35, 61; 525/363; 514/887, 514/494; 602/47, 43
See application file for complete search history.

(56) References Cited

U.S. PATENT DOCUMENTS

| | | | | |
|---|---|---|---|---|
| 3,987,000 A | * | 10/1976 | Gleichenhagen et al. ... | 523/111 |
| 5,041,287 A | * | 8/1991 | Driggers et al. ............... | 424/81 |
| 5,632,727 A | * | 5/1997 | Tipton et al. .................. | 602/47 |
| 5,708,023 A | * | 1/1998 | Modak et al. ............... | 514/494 |
| 5,725,491 A | * | 3/1998 | Tipton et al. .................. | 602/43 |
| 6,183,770 B1 | * | 2/2001 | Muchin et al. ............. | 424/448 |

\* cited by examiner

*Primary Examiner*—Sreeni Padmanabhan
*Assistant Examiner*—Gina Yu
(74) *Attorney, Agent, or Firm*—Sughrue Mion, PLLC

(57) ABSTRACT

Non-aerosol spray-on skin patch compositions as described comprising at least one substantially water insoluble film forming agent, at least one film plasticizer agent, at least one water soluble compound, and at least one organic solvent, the composition forming a flexible, porous and physiologically compatible skin patch when sprayed on to skin and allowed to dry. Also described are methods of improving wound healing by administering a physiologically active ingredient to a patient in need of such treatment.

17 Claims, No Drawings

COMPOSITIONS AND METHODS

FIELD OF THE INVENTION

The present invention relates to a non-aerosol spray-on skin patch composition and methods of using it in improving wound healing, and/or administering a physiologically active ingredient to a patient. The invention also relates to a spray on skin patch drug delivery system. Other aspects of the invention will become apparent from the description that follows.

BACKGROUND OF THE INVENTION

Although there are several skin patch compositions available on the market, which can be used for forming a protective film over a wound, they are associated with a number of problems. The spray-on skin patches presently known basically take the form of a water insoluble polymer dissolved in an organic solvent, with an appropriate propellant that will allow it to be applied in an aerosol form. A significant disadvantage with such compositions is that after being applied to the skin and being left to dry a non-porous film structure is formed that prevents the passage across it of gasses or moisture. The failure to allow moisture to move away from the wound results in excess moisture being trapped beneath the film surface causing depredation of the wound, and the possibility of infection.

It is also problematic that due to delivery via an aerosol means with the aid of a propellant, the spray-on skin patch is applied at a high pressure and can cause pain or discomfort to the patient when applied to a wound area. It has previously not been thought possible to eliminate the propellant from such compositions in order that the composition can be administered under lower pressure, the reason being that it was generally believed the presence of propellant was essential to prevent the clogging of the spraying nozzle through which the composition is applied.

Use of known spray-on skin patch composition has also been demonstrated in the past to allow the growth of microorganisms beneath the film covering that can lead to wound infection as indicated above.

The prevention or treatment of local or topical disease states or conditions of the skin has traditionally used simple non-occlusive delivery systems. These drug delivery systems usually include a volatile and/or non-volatile medium where a composition of the drug and medium is topically applied to the skin, in the vicinity of or directly on the area of skin to be treated. These delivery systems usually take the form of emulsion, creams, ointments, foams, gels, liquids, sprays and aerosols. Such delivery systems are generally used to treat skin inflammations, fungal and bacterial topical infection, soft-tissue contusions, parasites and topical analgesia. The limitation with this type of delivery system is that systemic drugs are generally not suitable for this type of administration, due to various factors possibly including the short interval of application. Some major problems with the current state of the art relate to a lack of efficacy of systemic drugs because of the low drug flux across the skin, inability to adequately control the rate of drug delivery, or the requirement for a very large application area. Problems with the poor dermal penetration of drugs is that the drug can be easily washed off, or transferred to clothes, other surfaces.

The dermal delivery of drugs may represent one of the oldest form of drug delivery in human history. Resins and animal fats were probably used by humans in early times to treat damage to the skin resulting from injuries and burns. Such substances for local delivery of active substances remained largely unchanged until as late as this century. The concept of transdermal systemic drug delivery was first seriously advocated by Dr. Alejandro Zaffaroni, for example, in U.S. Pat. Nos. 3,598,122 and 3,731,683 from the early 1970s. Transdermal systemic drug delivery provides an effective method of achieving improved bioavailability for physiologically active substances where the drugs are poorly absorbed by traditional routes of delivery, and/or when oral dosing is poorly tolerated or not possible.

Transdermal formulations are however limited. For example, polar drugs tend to penetrate the skin too slowly. Since most drugs are of a polar nature this limitation is significant, as is the fact that many drugs cause irritation at the site of topical application.

One common method known for assisting the rate of penetration of drugs across the skin is to increase the thermodynamic activity of the drug. The thermodynamic activity of a drug is proportional to the concentration of the drug and the selection of the vehicle. According to the laws of thermodynamics, the maximum activity of a drug is related to that of the pure drug crystal.

From the 1970s a principal focus of transdermal systemic drug delivery has been, and remains, on transdermal patch devices. These patch devices are like bandages which are attached to the surface of intact skin for prolonged periods of time to allow a desired systemic delivery of a drug or other physiologically active agent. These transdermal patch devices occlude the skin and trap the drug, together with volatiles and vehicle excipients, between the skin and an outer impermeable backing membrane. The membrane prevents the evaporation or diffusion of vehicle excipients, volatiles and drag into an environment other than the specific target skin site. The prolonged length of time required for transfer of the drug and excipients from the patch into the skin often results in local skin irritation. The irritation is caused by prolonged contact on the skin by the drug, volatiles, vehicle excipients, or the adhesive used to attach the patch device to the skin. The occlusive nature of the patch device also restricts the natural ability of the skin to "breathe", this being uncomfortable and increasing the risk of irritation. With added problems of complex and costly manufacturing processes for transdermal patch devices there is a need for improved transdermal drug delivery systems which allow ease of administration, simple preparation and comparatively low cost preparation.

The thermodynamic activity of a drug can be increased by employing supersaturated systems which give rise to unusually high thermodynamic potentials (Coldman, et al, *J. Pharm Sci.* 58(9): 119, 1969). However, topical vehicles relying on supersaturation have the major limitation of formulation instability, both prior to and during application to the skin. As such, they are of limited clinical value within a non-occlusive volatile:non-volatile delivery vehicle, because as soon as the formulation comes into contact with a person's clothing or the like, the drug often precipitates; hence the formulation is no longer supersaturated and any enhanced percutaneous absorption ceases.

Other workers such as Kondo, et al (*J. Pharmacobio-Dyn.*, 10:743 1987) who were using supersaturation to achieve enhanced transdermal drug delivery, have relied on the use of anti-nucleating polymers to stabilize the formulation. However, the applied drug formulations stabilized with polymers formed an appreciable surface mass on the skin which remained there over a prolonged duration of many hours, not a few minutes. So, while Kondo advocated the use of a metered spray to deliver these formulations, in reality it would be impossible to obtain a non-occlusive delivery system with a short application time and still maintain a clinically useful transdermal penetration enhancement.

It is accordingly an object of the present invention to provide a spray-on skin patch composition that overcomes some of the problems associated with prior art compositions and systems. Other objects of the present invention will become apparent from the following detailed description.

SUMMARY OF THE INVENTION

According to one embodiment of the present invention there is provided a non-aerosol spray-on skin patch composition comprising:
  (a) at least one substantially water insoluble film forming agent;
  (b) at least one film plasticiser agent;
  (c) at least one water soluble compound; and
  (d) at least one organic solvent;

the composition forming a flexible, porous and physiologically compatible skin patch when sprayed onto skin and allowed to dry.

The composition may also include a physiologically active ingredient or pro-drug thereof for application to a wound site.

According to another embodiment of the invention there is provided a spray patch skin delivery composition comprising:
  (a) at least one substantially water insoluble film forming agent;
  (b) at least one film plasticiser agent;
  (c) at least one water soluble compound;
  (d) at least one organic solvent; and
  (e) one or more physiologically active ingredient or a pro-drug thereof;

the composition forming a flexible, porous and physiologically compatible skin patch when sprayed onto skin and allowed to dry, and which provides transdermal drug delivery.

According to another aspect of the invention there is provided a spray patch transdermal drug delivery system which comprises at least one physiologically active agent or pro-drug thereof in a water insoluble, porous, film structure containing drug depots.

According to a still further embodiment of the present invention there is provided a method of improving wound healing or administering a physiologically active ingredient to a patient in need of such treatment comprising applying to a wound or to skin of the patient an effective amount of a composition as referred to above.

Other aspects of the invention are described hereinafter.

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

By the term "non-aerosol" it is intended to mean that the composition does not comprise a propellant that will serve to deliver it under pressure. By way of example, the composition may conveniently be applied from a pump-pack type of dispensing container that will utilise the pumped influx of air to force the composition out through a spraying nozzle, under relatively low pressure.

There are several aspects to the invention. In one main aspect the skin patch composition is adapted to be sprayed onto a wound, such as for example a cut, sore, abrasion, burn or other affected part of the skin. In another aspect, a spray patch skin delivery composition is adapted to be applied to normal skin as a means of delivering to or through the skin (transdermally) of the patient a physiologically active ingredient such as systemically active drug, or prodrug thereof. In such cases the spray-on skin patch composition will preferably be delivered/administered in a metered dose.

In a first aspect of the invention the composition comprises at least one substantially water insoluble film forming agent, at least one film plasticiser agent, at least one water soluble compound and at least one organic solvent. The ingredients should of course be physiologically compatible and when combined, administered to the skin and allowed to dry the composition forming a flexible, and physiologically compatible porous, skin patch or skin covering film which degrades over time.

The film forming agents that may be used in the present invention include acrylic acid and its derivatives, polyacrylic and its derivatives such as polybutylmethacrylate and polymethacrylic acid, polymethacrylate, ascorbyl palmitate, carbomer, carnauba wax, cellulose derivatives such as cellulose acetate phthalates, rosca mellose sodium, hydroxyethyl cellulose, hydroxypropyl cellulose, hydroxypropyl methylcellulose, ethyl cellulose and related compounds, hydroxypropyl methylcellulose phthalate, hypromellose phthalate, crospovidone and derivatives/related compounds, cetyl alcohol and derivatives, microcystalline wax, poloxamer, polyethylene glycol, polyurethane, polyvinyl acetate, polyvinyl acetate phthalate, polyvinyl alcohol, povidone, silicone rubber and derivatives, shellac, triglycerides derivatives. These film forming agents are organic solvent soluble, for example, in organic solvents which are dermatological compatible solvents used in dermatological, pharmaceutical and veterinary applications.

It is also possible for a number of substantially water insoluble film forming agents to be included within the composition, which when combined and applied to the skin will likewise form a flexible skin patch.

The composition should include at least one film plasticiser agent that will serve to soften the polymer film formed by the film forming agent and to ensure that it is sufficiently flexible that it can move with the skin on the area to which it is applied without cracking and peeling (at least during the intended lifespan of the skin patch). Examples of suitable film plasticiser agents include polybutylphthalate, benzyl benzoate, dibutyl sebacate, dimethyl phthalate, dibutyl phthalate, triacetin, glycol and derivatives thereof, benzyl benzoate, glycerin, mineral oil, lanolin alcohols (such as $C_{1-8}$ alcohols), petroleum and lanolin alcohols, polyethylene glycol, glycerin, sorbitol, triacetin, triethylene citrate, propylene glycol, chlorbutanol, castor oil and gelatin.

An important aspect of the present invention is that the skin patch formed by use of the composition is porous. This porosity is achieved by including within the composition at least one water soluble compound that will be integrated within the polymer film when applied to the skin. Without limiting the invention, it is believed that the presence of a water soluble compound will, when the film comes into contact with moisture, cause molecules of this compound to leach out of the film, resulting in the forming of windows or pores within the film itself. These pores will allow the passage of gases and water vapour through the skin patch film. In a preferred embodiment of the invention the water soluble compound also has another role within the composition, such as for example as a physiologically active ingredient. Examples of physiologically active ingredients that are also water soluble include antimicrobial quaternary ammonium compounds such as for example cetrimide alkylaryltrialkylammonium chloride, alkylaryltrimethylammonium chloride, amantanium bromide, benzalkonium chloride, benzethonium chloride, benzododecinium bromide, cetalkonium chloride, cethexonium bromide, cetrimonium bromine, and cetyldimethylethylammonium bromide.

Compounds such as these will integrate evenly within the film and act immediately on bacteria associated with the effected skin area covered by the film, leaving a multiplicity of windows or pores within the film, allowing the skin beneath to breathe and perspire, and at the same time preventing the trapping of anaerobic bacteria beneath the film. Quaternary ammonium compounds such as cetrimide are advantageous because they have surfactant action which may assist in binding the film onto the skin to which it is applied. Quaternary ammonium compounds such as cetrimide may also assist to soften and maintain the softness of blood clots with which it will come into contact. This action helps to prevent scabbing of a wound, cut or abrasion, thus facilitating the antimicrobial effects.

Other examples of water soluble compounds that can be incorporated within the composition to aid in formation of pores within the skin patch are antifungal agents such as chlorbutanol, phenol, phenol derivatives such as resorcinol, salicylic acids, acrisorcin, amorolfine, amphotericin, azoles derivatives and related compounds (bifonazole, butoconazole nitrate, chlormidazole, clotrimazole, croconazole, econazole, enilconazole, fenticonazole, fluconazole, flutrimazole, isoconazole, itraconazole, ketoconazole, lanoconazole, miconazole, omoconazole, saperconazole, sertaconazole, sulconazole, terconazole, tioconazole), benzoyl disulphide, bromochlorosalicylanilide, buclosamide, butenafine, candicidicaprylic acid, chlorphenesin, ciclopirox olamine, cilofingin, fenticlor, flucytosine, criseofulvin, hachimycin, haloprogin, hamycin, hydroxystilbamidine isethionate, loflucarban, mepartricin, natamycin, nifuroxime, p-nitrophenol, nystatin, pentamycin, propionic acid protiofate, pyrrolnitrin, sulbentine, terbinafine, tolciclate, tolnaftate, tiacetin, undecenoic acid. Water soluble agents are not limited to antimicrobial agents or antifungal agents. Skin conditioners such as ethoxylated lanoline, alcohols (such as $C_4$ to $C_8$ alcohols, for example, methanol, ethanol, propanol or isopropanol), and glycerin may be used. Any material that has good solubility in water and slight solubility in volatile organic solves such as such as $C_4$ to $C_8$ alcohols (for example, methanol, ethanol, propanol or isopropanol), acetone, ethyl acetate, dimethyl ether and other polar solvents may also be used.

In order to aid application of the skin patch composition by spraying, the composition will include at least one organic solvent, preferably a volatile organic solvent. By way of example only, one or more solvents may be selected from acetone, ethyl acetate and isopropanol. These solvents are preferred as they may offer some bactericide activity. Other solvents that may be adopted include: alcohols, for example $C_{1-10}$ alcohols, such as benzyl alcohol, ethanol, methanol, butanol, isobutanol, diacetone alcohol; chlorinated hydrocarbons such as methylene chloride, carbon tetrachloride, trichloroethylene, chlorothene SM; esters such as methyl acetate, ethyl acetate, n-propyl acetate, n-butyl acetate, isobutyl acetate, amyl acetate, 2-thyl hexyl acetate, duPont DBE, Exxate 500, 700, 900; glycol and ether/ester derivatives, ethylene glycol, PM acetate, butyl celluosolve, Carbritol acetate, butyl Carbritol acetate, Ektapro EEP; hydrocarbons such as toluene, eyxlene, VM&P naphtha, mineral spirits, Aromatic 100, Aromatic 150, ketones such as acetone, methyl ethyl ketone, methyl butyl ketone; ethers such as dimethyl ether; benzyl benzoate; isoptopyl myristate; acetonitrile; ethyl oleate; glycerol, glycofurol (tetraglycol); propylene glycol, polyethylene glycol (PEG); bexane; n-hexane, glycol ethers; methylene chloride; methyl chloride; octyl dodecanol; toluene; trichlorethane; diethyl phthalate; and dibutyl phthalate. These solvents are volatile and, in general, in levels used in dermatological preparations do not cause substantial irritation to the skin, that is, are pharmaceutically acceptable. On application to the skin the solvents rapidly volatilize. A small amount of a non-volatile solvent (for example, less than 2% v/v of total solvent) may be included.

The spray-on skin patch composition having wound treatment application may optionally include one or more physiologically active ingredients, or prodrugs thereof, that may for example be one or more of, or a combination of the following: rapidly-acting antimicrobials (such as cetrimide), long-acting antimicrobials, such as triclosan, benzyl benzoate, dibutyl sebacate, dimethyl phthalate, dibutyl phthalate, tiacetin, glycol and derivatives, cortico steroids, pain relieving agents, compounds having antiinflammatory activity, antihistamine, and biologically active peptides or proteins. This list of active agents is not intended to be limiting upon the nature of physiologically active ingredients that can be incorporated within such compositions as any agents that are compatible with the other components of the composition and which can be administered effectively via spraying onto the skin are considered to fall within this aspect. Details of physiologically active ingredient which may be used in this aspect are set out below in relation to the spray patch skin delivery composition aspect of the invention.

By the terms "rapidly-acting" and "long-acting" antimicrobials as used herein it is envisaged that short-acting antimicrobials will effect an anti-microbial activity at the site of application for a period of between about one and about four hours, whereas long-acting antimicrobials will demonstrate activity over a period of from about four hours to about forty eight hours. Activity can be measured by methods routine in the art, that involve taking a swab from a wound site and monitoring microorganism proliferation and viability following exposure to the anti-microbial concerned.

Where the water soluble component of the composition is a physiologically active ingredient, the optional one or more physiologically active ingredient may be the same or different.

In accordance with another aspect of the invention there is provided a spray patch skin delivery composition comprising:
 (a) at least one substantially water insoluble film forming agent;
 (b) at least one film plasticiser agent;
 (c) at least one water soluble compound;
 (d) at least one organic solvent; and
 (e) one or more physiologically active ingredient or a prodrug thereof;

the composition forming a flexible, porous and physiologically compatible skin patch when sprayed onto skin and allowed to dry, and which provides transdermal drug delivery.

The physiologically active agent or prodrug thereof which may be used in this aspect includes any locally or systemically active agents which are compatible with the porous film of the invention. These agents may be delivered transdermally through the skin without the need for dermal penetration enhancers (which may cause skin irritation or sensitivity). Examples of physiologically active agents or prodrugs thereof include, one or more conveniently classified below by therapeutic class.

Alimentary System

Antidiarrhoeals such as diphenoxylate, loperamide and hyoscyamine.

Cardiovascular System

Antihypertensives such as hydralazine, minoxidil, captopril, enalapril, clonidine, prazosin, debrisoquine, diazoxide, guanethidne, methyldopa, reserpine, trimetaphan.

Calcium channel blockers such as diltiazem, felodopine, amlodipine, nitrendipine, nifedipine and verapamil.

Antiarrhyrthmics such as amiodarone, flecainide, disopyramide, procainamide, mexiletene and quinidine.

Antiangina agents such as glyceryl trinitrate, erythritol tetranitrate, pentaerythritol tetranitrate, mannitol hexanitrate, perhexilene, isosorbide dinitrate and nicorandil.

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate.

Cardiotonic glycosides such as digoxin and other cardiac glycosides and theophylline derivatives.

Adrenergic stimulants such as adrenaline, ephedrine, fenoterol, isoprenaline, orciprenaline, rimeterol, salbutamol, salmeterol, terbutaline, dobutambe, phenylephrine, phenylpropanolamine, pseudoephedrine and dopamine. Vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol. Antimigraine preparations such as ergotamine, dihydroergotamine, methiysergide, pizotifen and sumatriptan.

Drugs Affecting Blood and Haemopoietic Tissues.

Anticoagulants and thrombolytic agents such as warfarin, dicoumarol, low molecular weight heparins such as enoxaparin; plasminogen activators such as streptokinase and its active derivatives, t-pA and its derivatives and the like.

Haemostatic agents such as aprotinin, tranexamic acid and protamine.

Central Nervous System

Analgesics, antipyretics including the opiod analgesics such as buprenorphine, dextromoramide, dextropropoxyphene, fentanyl, alfentanil, sufentarlil, hydromorphone, methadone, morphine, oxycodone, papaveretum, pentazocine, pethidine, phenoperidine, codeine and dihydrocodeine. Others include acetylsalicylic acid (aspirin), paracetamol, and phenazone.

Hypnotics and sedatives such as the barbiturates, amylobarbitone, butobarbitone and pentobarbitone and other hypnotics and sedatives such as choral hydrate, chlormethiazole, hydroxyzine and meprobamatc.

Antianxiety agents such as the benzodiazepines, alprazolam, bromazepam, chlordiazepoxide, clobazam, chlorazepate, diazepam, flunitrazepam, flurazepam, lorazepam, nitrazepam, oxazepam, temazepam and triazolam.

Neuroleptic and antipsychotic drugs such as the phenothiazines, chlorpromazine, fluphenazine, pericyazine, perphenazine, promazine, thiopropazate, thioridazine and trifluoperazine and the butyrophenones, droperidol and haloperidol and the other antipsychotic drugs such as pimozide, thiothixene and lithium.

Antidepressants such as the tricyclic antidepressants amitryptyline, clomipramine, desipramine, dothiepin, doxepin, imipramine, nortriptytine, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline.

CNS stimulants such as caffeine.

Antialzheimer's agents such as tacrine.

Antiparkinson agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923).

Anticonvulsants such as phenytoin, valproic acid, primidone, phenobarbitone, methylphenobarbitone and carbamazepine, ethosuximide, methsuximide, phensuximxde, sulthiame aid clonazepam Antiemetics, antinauseants such as the phenothiazines, prochloperazine, thiethylperazine and 5HT-3 receptor antagonists such as ondansetron and granisetron and others such as dimenhydrinate, diphenhydramine, metoclopramide, domperidone, hyoscine, hyoscine hydrobromide, hyoscine hydrochloride, clebopride and brompride.

Musculoskeletal System

Non-steroidal antiinflammatory agents including their racemic mixtures or individual enantiomers where applicable, such as ibuprofen, flurbiprofen, ketoprofen, aclofenac, diclofenac, aloxiprin, aproxen, aspirin, diflunisal, fenoprofen, indomethacin, mefenarnic acid, naproxen, phenylbutazone, piroxicam, salicylamide, salicylic acid, sulindac, desoxysulindac, tenoxicam, tramadol and ketoralac.

Additional non-steroidal antiinflammatory agents which can be formulated in combination with the dermal penetration enhancers include salicylamide, salicylic acid, flufenisal, salsalate, triethanolamine salicylate, aminopyrine, antipyrine, oxyphenbutazone, apazone, cintazone, flufenamie acid, clonixeril, clonixin, meclofenarnie acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxul, fenbufen, cinchophen, diflumidone sodium, fenamole, flutiazin, metazrnide, letimide hydrochloride, nexeridine bydrochloride, octazamide, molinazole, neocinchophen, niazole, proxazole citrate, tesicam, tesimide, tolmetin, and triflumidale.

Antirhoumatoid agents such as penicillamine, aurothioglucose, sodium aurothiomalate, methotrexate and auranofin.

Muscle relaxants such as baclofen, diazepam, cyclobenzaprine hydrocblotide, dantrolene, methocarbamol, orphenadrine and quinine.

Agents used in gout and hyperuricaemia such as allopurinol, colchicinc, probenecid and sulphinpyrazone.

Hormones and Steroids

Oestrogens such as oestradiol, oestriol, oestrone, ethinyloestradiol, rnestranol, stilboestrol, dienoestrol, epioestriol, estropipate and zeranol.

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol.

Antiandrogens such as cyproterone acetate and danazol.

Antioestrogens such as tamoxien and epitiostanol and the aromatase inhibitors, exemestane and 4-hydroxy-androstenedione and its derivatives.

Androgens and anabolic agents such as testosterone, methyltestosterone, clostebol acetate, drostanolone, furazabol, nandrolone oxandrolone, stanozolol, trenbolone acetate, dihydrotestosterone, 17-alpha-methyl-19-nortestosterone and fluoxymesterone 5-alpha reductase inhibitors such as finasteride, turosteride, LY-191704 and MK-306.

Corticosteroids such as betamethasone, betamnethasone valerate, cortisone, dexamethasone, dexamethasone 21-phosphate, fludrocortisone, flunethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, tiamcinolone, triameinolone acetonide.

Further examples of steroidal antiinflammatory agents for use in the instant compositions include cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flumnsolide, tlucortolone, fluoromehalone, fluparulone, fluprednisolone, meprcdnisone, methylmeprieisolone, paamethasone, cortisone acctate, hydrocortisone cyclopentylpropionate, cortodoxone, flucetonide, fludrocottisone acetate, flurandrenolone acetonide, medrysone, amcinafal, amcinafde, betamethasone, betamethasone benzoate, chloroprednisone acetate, clocortolone acetate descinolone acctonide, desodnmetasone, dichlorisonc acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol. Pituitary hormones and their active derivatives or analogs such as corticotrophin, thyrotropin, follicle stimulating hormone (FSH), luteinising hormone (LH) and gonadotrophin releasing hormone (GnRH).

Hypoglycaemic agents such as insulin, chlorpropamide, glibenclamide, gliclazide, glipizide, tolazanide, tolbutamide and metformin.

Thyroid hormones such as calcitonin, thyroxine and liothyronine and antithyroid agents such as carbimazole and propylthiouracil.

Other miscellaneous hormone agents such as octreotide.

Pituitary inhibitors such as bromocriptine.

Ovulation inducers such as clomiphene.

Genitourinary System

Diuretics such as the thiazides, related diuretics and loop diuretics, bendrofluazide, chlorotwiazide, chlorthalidone, dopamine, cyclopenthiazide, hydrochlorothiazide, indapramide, mefuside, meiycholthiazide, metolazone, quinethazone, bumetanide, ethacrynic acid and frusemide and potassium sparing diuretics, spironolactone, amiloride and triamterene.

Antidiuretics such as desmopressin, lypressin and vasopressin including their active derivatives or analogs.

Obstetric drugs including agents acting on the uterus such as ergometrine, oxytocin and gemeprost.

Prostaglandins such as alprostadil (PGE1), prostacyclin (PGI2), dinoprost (prostaglandin F2-alpha) and misoprostol.

Antimicrobials

Antimicrobials including the cephalosporins such as cephalexin, cefoxytin and cephalothin.

Penicillins such as amoxycillin, amoxycillin with clavulanic acid, ampicillin, bacampicillin, benzathine penicillin, benzylpenicillin, carbenicillin, cloxacillin, methicillin, phenetbicillin, phenoxymethylpenicillin, flucloxacillin, mezlocillin, piperacillin, ticarcillin and azlocillin.

Tetracyclines such as iminocycline, chlortetracycline, tetracycline, demeclocycline, doxycycline, methaycline and oxytetracycline and other tetracycline-type antibiotics.

Aminoglycosides such as amikacin, gentamicin, kanamycin, neomycin, netilmicin and tobramycin.

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, tiacetin, zinc, pyrithione and sodium pyrithione. Quinolones such as nalidixie acid, cinoxacin, ciprofloxacin, enoxacin and norfloxacin. Sulphonamides such as phthalylsulphthiazole, sulfadoxine, sulphadiazine, sulphamethizole and sulphametboxazole.

Sulphones such as dapsone.

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycrin, nitrofurantoin, spectinomycin, vancomycin, aztreonam, colistin IV, metronidazole, tinidazole, fusidic acid and trimethopinm; 2-thiopyridine N-oxide; halogen compounds, particularly iodine and iodine compounds such as iodine-PVR complex and diiodohydroxyquin; hexachlorophene; chlorhexidine; chloroamine compounds; benylperoxide.

Antituberculosis drugs such as ethambutol, isonizid, pyrazinamide, rifampicin and clofazimine.

Antimalarials such as primaquine, pyrimethamine, chloroquine, hydroxychloroquine, quinine, mefloquine and halofantrine.

Antiviral agents such as acyclovir and acyclovir prodrugs, famciclovir, zidovudine, didanosinc, stavudine, lamivudine, zalcitabine, saquinavir, indinavir, ritonavir, n-docosanol, tromantadine and idoxuridine.

Anthelmintics such as mebendazole, thiabendazole, niclosamide, praziquantel, pyrantel embonate and diethylcarbamrazne.

Cytotoxic agents such as plicamycin, cyclophosphamide, dacarbazine, fluorouracit and its prodrugs (described, for example, in *International Journal of Pharmceutics* 111: 223–233 (1994)) methotrexate, procarbazine, 6-mercaptopurine and mucophenolic acid.

Antiseptics

Still other antimicrobial or antiseptic agents which may be used include alcohols such as ethanol, isopropanol and methylated spirit; cationic surfactants such as quaternary ammonium compounds, benzalkonium chloride, cetrimide, cetypyridinium chloride, bisdequalinium diacetate, and dequalinium chloride; bisbiguanides such as chlorhexidine and its salts such as chlorhexidineacetate, and polymeric biguanides such as PMMB; chlorine or chlorine containing agents such as chloramine, sodium dichloroiseyanuate and sodium hypochlorite; dyes such as acridinc derivatives, brilliant green, crystal violet, magenta and malachite green; iodophores such as providone-iodine; mercurials such as chiomersal and mercurochrome; oxidising agents such as hydrogen peroxide, peracetic acid and potassium permanganate; phenoxyethanol; phenethyl alcohol; and phenols such as chlorocresol, chloroxylenol, cresol, chlorophenol (triclosane), hexachlorophane and phenol.

Metabolism

Anorectic and weight reducing agents including dexfedfluraminc, fenflurainine diethylpropion, mazndol and phentermine.

Agents used in hypercalcaemia such as calcitriol, dihydrotachysterol and their active derivatives or analogs.

Respiratory System

Antitussives such as ethylmorphine, dextromethorphan and pholcodine.

Expectorants such as acetylcysteine, bromhexine, emetine, guaiphenesin, ipecacuanha ans saponins.

Decongestants such as phenylephrine, phenylpropanolamine ans pseudoephedrine.

Bronchospasm relaxants such as ephedrine, fenoterol, orciprenaline, rimiterol, salbutamol, sodium cromoglyeate, cromoglycic acid and its prodrugs (described, for example, in *International Journal of Pharmaceutics* 7:63–75 (1980)), terbutaline, ipratropium bromide, salmeterol and theophylline and theophylline derivatives.

Allergy and Immune System

Antihistamines such as meclozine, cyclizine, chiorcyclizine, hydroxyzine, brompheniramine, chlorpheniramine, clemastine, cyproheptadine, dexchlorpheniramine, diphenhydramine, diphenyle, doxylamine, mebhydrolin, mepyramine, pheniramine, tripolidine, azatadine, diphenylpyraline, methdilazine, terfexine, astemizole, loratidine and cetirizine.

Local anaesthetics such as bupivacaine, amethocaine, lignocaine, cinchocaine, dibucaine, mepivacaine, prilocalne and etidocaine.

Stratum corneum lipids, such as ceramides, cholesterol and free fatty acids, for improved skin barrier repair (Man, et al, *J. Invest. Dermatol.,* 106(5):1096, 1996).

Neuromuscular blocking agents such as suxamcthonium, alcuronium, pancuronium, atracurium, gallie, tubocurarinre and vecuronium.

Smoking cessation agents such as nicotine, bupropion and ibogaine.

Insecticides and other pesticides which are suitable for local or systemic application.

Dermatological agents, such as vitamins A and E, vitamin E acetate and vitamin E sorbate.

Allergens for desensitization such as house dust mite allergen.

Nutritional agents, such as vitamins, essential amino acids and essential fats.

Keratolytics such as the alpha-hydroxy acids, glycolic acid and salicylic acid.

Psychicenergisers, such as 3-(2-aminopropyl)indole, 3-(2-aminobutyl)indole, and the like.

Anti-acne agents such as containing isotretinoin, tretinoin and benzoyl peroxide.

Anti-psoriasis agents such as containing etretinate, cyclosporin and calcipotriol.

Anti-itch agents such as capsaicin and its derivatives such as nonivamide (Tsai, et al, *Drug. Dev. Ind. Pharm.,* 20(4): 719, (1994)).

Anticholinergic agents, which are effective for the inhibition of axillary sweating and for the control of prickly heat. The antiperspirant activity of agents such as methatropine nitrate, propantheline bromide, scopolamine, methscopolamine bromide, and the new class of soft antiperspirants, quaternary acyloxymethyl ammonium salts (described, for example, by Bodor et al, *J. Med. Chem.,* 23:474 (1980) and also in United Kingdom Specification No 2010270, published 27 Jun. 1979).

Other physiologically active peptides and proteins, small to medium-sized peptides, for example, vasopressin and human growth hormone.

The physiologically active agent or a prodrug thereof is preferably present at a concentration which is soluble in the delivery system, but after evaporation of solvent may precipitate forming drug depots in the porous film.

A concentration gradient is believed, without wished to be bound by theory, to be the means through which biologically agents or prodrugs thereof pass through the skin. It is believed that the porous nature of the patch or film which forms on the skin provides a depot like effect with foci of highly concentrated biologically active agents. The concentration gradient so formed is believed to force the agent across the skin. A continuous delivery may result. It is also believed that the porous nature of the film, which allows the passage of gases and water vapour, and avoids issues of skin irritation associated with films/patches applied to the skin for transdermal application.

An advantage of the compositions according to the present invention is that hey may disintegrate over a period of time so that peeling or scrubbing off of the film may be unnecessary. The time frame of such disintegration is governed by the choice of the film forming agent and the degree of interruption within the film that has been caused by addition to the composition of a water soluble compound. By selection of these components the lifespan of the skin patch can be varied as a design feature of the composition. For example, the patch may disintegrate over say a twenty four or forty eight hour time period.

In another aspect of the invention there is provided a spray patch transdermal drug delivery system which comprises at least one physiologically active agent or pro-drug thereof in a water insoluble, porous, film structure containing drug depots.

The drug delivery system is adapted to transport the physiologically active agent across a dermal surface or mucosal membrane of an animal, including a human. The device is of low toxicity to, and is exceptionally well tolerated by the dermal surface or mucosal membrane of the animal.

The present invention also provides a method for administering at least one systemic or locally acting physiologically active agent or prodrug there of to an animal which comprises applying an effective amount of the physiologically active agent in the form of a composition or a drug delivery system according to the present invention.

Preferably the animal is a human but the invention also extends to the treatment of non-human animals, such as companion animals (for example, dogs and cats), domestic animals, for example, cows/cattle, sheep, horses, goats, pigs and the like, and birds.

Surprisingly, the compositions and device of the invention enhances the absorption of active agents and prodrugs thereof through the skin and mucous membranes while avoiding the significant pharmacological disadvantages and toxicities of prior art approaches.

In the compositions and drug delivery systems according to the various aspects of the invention a pharmaceutical compounding agent, cosolvent, surfactant, emulsifier, antioxidant, preservative, stabilizer, diluent or a mixture of two or more of said components may be incorporated as is appropriate to the particular route of administration and dosage form. The amount and type of components used should be compatible with the polymer film structure. A cosolvent, or other standard adjuvant such as a surfactant, may be used to maintain a physiologically active agent, or prodrug, thereof in a solution or suspension at the desired concentration.

The pharmaceutical compounding agents can include paraffin oils, esters such as isopropyl, myristate, ethanol, silicone oils and vegetable oils. These are preferably used in the range of greater than 1%. Surfactants such as ethoxylated fatty alcohols, glycerol monostearate, phosphate esters, and other commonly used emulsifiers and surfactants preferably in the range of 0.1% to 1% may be used, as may be preservatives such as hydroxybenzoate esters for preservation of the compound preferably in amounts of 0.01% to 0.5%. Typical cosolvents and adjuvants may be ethyl alcohol, isopropyl alcohol, acetone, dimethyl ether and glycol ethers such as diethylene glycol monoethylether. These may be used in amounts of 1% to 90%.

When a pharmaceutical compounding agent, cosolvent, surfactant, emulsifier, antioxidant, preservative, stabilizer, diluent or a mixture of two or more of said components is used, these must be compatible with the ability of the system to become touch-dry after application.

The non-aerosol spray-on skin patch compositions according to the invention can conveniently be applied by means of a positive displacement metered dose hand pump, preferably having a lock down device that will seal the entry of air into the can. The organic solvents included within the composition will serve to clean the spraying nozzle and prevent build up of polymer film there within. By using the metered dose pump it is possible to deliver a precise amount of film onto the skin, and this in association with knowledge of the concentration of physiologically active ingredients within the composition can serve to ensure that the level of active administered is tightly controlled. Other variables that will need to be considered in the control of active ingredient administration (especially in the situation where the dose application is not metered) include the area of skin contacted with the composition, and the length of time of skin contact. Naturally, it will be well within the capabilities of a skilled physician to determine the effective amount of the physiologically active ingredient that needs to be applied, as well as the number of applications required, and alter the variables mentioned above in order to ensure the correct level of administration. Factors that would be apparent to a skilled clinician such as the height, weight, age, sex and general state of health of the patient concerned may also need to be considered, in determining the correct dose for a specific patient. For example, dosage ranges may include an active ingredient in the range from about 0.01 ng to 500 mg, such as 0.01 mg to 100 mg, for example 0.1 mg to 75 mg or 1 mg to 300 mg per dose.

Proportions of the components, according to various aspects of this invention, include, but are not limited to, 1% to 50% w/w film forming agent, 0.1% to 20% w/w film plasticiser agent, 0.01% to 10% w/w water soluble compound or compounds, and 30% to 90% w/w organic solvent or solvents.

In one embodiment the skin delivery composition may comprise a non-aerosol spray-on skin patch composition comprising:

0.01% to 10% w/w of one or more water soluble compounds 0.01% to 10% w/w of one or more physiologically active ingredient/s 1% to 50% w/w of polymethacrylic acid 0.1% to 20% w/w of polybutylphthalate 0% to 90% w/w of isopropanol 0% to 90% w/w of acetone ethylacetate up to 100% w/w, the composition forming a flexible, porous and physiologically compatible skin patch when sprayed onto skin and allowed to dry.

Other physiologically acceptable carriers, diluents, solvents or excipients may also be included within the composition, as is well known in the art of pharmaceutical formulation.

Details of such materials are provided within *Max Remington's Pharmaceutical Sciences,* 17th Edition, Mack Publishing Co, Easton Pa., USA, the disclosure of which is included herein in its entirety, by way of reference.

The compositions according to the present invention may be used in methods of treatment, such as, for the treatment of skin wounds, fungal infection, healing after plastic surgery, eczema, bacterial infection in or on the skin and or associated with skin wounds, athlete's foot, skin ulceration, burns, scalds, insect bites, local analgesia, itching, pain, and other method aspects as herein described.

Pain treated herein may be rheumatic pain (such as joint and muscle pain), pain associated with skin ulcers, pain associated with anal fissure and the like.

Administration may be to the site of injury or condition, or remote thereto.

Further aspects of the present invention will be explained in the following non-limiting Examples.

EXAMPLES

Example 1

A composition is prepared as follows:

a non-aerosol spray-on skin patch composition comprising:

0.05% w/w of centrimide 0.07% w/w of triclosane 0.6% w/w of chlorbutanol

10% w/w of polymethacrylic acid 1.2% w/w of polybutylphthalate

4% w/w of isopropanol

24% w/w acetone ethylacetate up to 100% w/w.

Example 2

Continuous release of antimicrobial actives from the applied composition of Example 1

Sample

One liter of the compositions according to Example 1 (Spray On Antimicrobial Bandage) in a Nalgene bottle was received for validation. The bottle was labelled "Ref. BX258

Method

The procedure was based on the Australian Standards AS1157.1 and 0.2, 1998 incorporating the microbes stipulated in the BP Preservative Efficacy Test.

One mL of the sample was used to saturate a membrane pad. Once dry, the pad was then placed onto the surface of agar plates containing a lawn culture of the following microorganisms:

| Medium | Micro-organism | Challenge population/plate |
|---|---|---|
| *TSA | Escherichla coli | $3 \times 10^8$ |
| TSA | Staphylococcus aureus | $3 \times 10^8$ |
| *SDA | Candida albicans | $3 \times 10^6$ |
| SDA | Aspergillus niger (spores) | $1 \times 10^7$ |

(*TSA = Tryptone Soya Agar, SDA = Sabouraud Dextrose Agar)

Positive and negative controls were performed in parallel. The TSA plates were incubated at 37° C. for three days and the SDA plates were incubated at 25° C. for five days.

Results

Where

G=Growth evident on pad

NG=No growth evident on pad

After incubation growth was noted on the plate, pad and under the pad and any zone of inhibition was measured.

| | Pad G or NG/ |
|---|---|
| Micro-organism | Zone of Inhibition |
| E. coli: | NG/0.5 mm |
| S. aureus: | NG/0.5 mm |
| C. albicans: | NG/0.6 mm |
| A. niger: | NG/no zone of inhibition |

Findings

1. All surfaces coated with Medico Spray-On Bandage prevented microbial growth on the agar in contact with the product. This was irrespective of whether the field was—
   (a) *E. coli*, a Gram-negative bacterial rod
   (b) *S. aureus*, a Gram-positive bacterial coccus
   (c) *C. albicans*, a pathogenic yeast
   (d) *A. niger*, a spore-bearing mould
2. A zone of inhibition was noted in challenges (a) to (c) above, although this effect is not deemed necessary for the product; i.e—the spray-on bandage need only prevent growth in the region sprayed which covers the open wound. Efficacy beyond the zone of broken skin is independent of the functional application of the product.
3. Controls were in line with expectation, that is, uninhibited bacterial growth took place.

Example 3

Effect of Example 1 Composition on Contusion

This example shows that the composition of Example 1 is a transparent, antiseptic, waterproof, washable "Spray-on-Bandage" having application in cuts, minor wounds and abrasions. Effectiveness in an artificial contusion in the rabbit was studied. The following results were obtained.

1. The date of testing
   13 Jun. 1999 until 23 Jul. 1999
2. The testing materials and test method
   1) Testing animal: Rabbit.
   2) Testing composition: Example 1 composition.
   3) The two artificial wounds have been made on the centre of the back of the rabbits.
   Observations were taken after contusion on treated and non-treated animals.
   a) The operative method to make the artificial contusion
      Hair has been shaved on the centre part of rabbit's back, and then the intrusion of
      3 cm² made by strong abrasion to the skin with sandpaper.
   b) Observation
      The visible observation to the naked eye has been made on the first day, the second day, the fifth day and the tenth day respectively after the operation. On the tenth day the rabbit has been killed so that the inspection of pathological tissue can be made.
3. Result
   1) Visible Observation
      The visible change of the operated part is shown in the Table 1 below.

TABLE 1

| | Observation Items | $1^{st}$ day | $2^{nd}$ day | $5^{th}$ day | $10^{th}$ day |
|---|---|---|---|---|---|
| Treatment with Example 1 | Area of operated part (cm²) | 3 | 3 | 3 | 3 |
| | Redness | − | − | − | − |
| | Scabbing | − | − | − | − |
| | Hypertrophy | + | − | − | − |
| Without treatment | Area of operated part (cm²) | 1.7 | 1.7 | 1.3 | 1.0 |
| | Redness | − | − | − | − |
| | Scabbing | + | + | + | + |
| | Hypertrophy | − | + | ++ | +++ |

2) The inspection of the pathological tissue of the operated part Pathological tissue analysis is shown in Table 2

TABLE 2

| | Treated with Example 1 | Untreated object |
|---|---|---|
| Epidermis | normal | Increase |
| Papilla | normal | Extend |
| Papilla layer | normal | Increase |
| Scabbing formation | none | Exist |
| Cell infiltration | small | Big |

4. Conclusion
   1) As far as the visible observation is concerned, the untreated wound has scabbing on the first day after operation. Compression from the surrounding tissue is visible on the operated part. Furthermore, hypertrophy has been continuous.
      On the other hand, as to the wound treated with Example 1, we were unable to observe any atrophy on the operated part due to the performance of the composition
   2) Pathological tissue analysis of the untreated wound shows on the operated part, as to chronic dermatitis, increase of epidermis, increase of papilla layer, and cell infiltration.

On the contrary, as far as the specimen treated with Example 1 is concerned, no significant abnormality has been observed except for the slight cell infiltration.

Full protection of wounds as well as the regeneration of normal tissue is observed with the treatment composition.

Plastic surgery tissue abrasions may be treated with the composition. Other examples of application include bandages for the wounds to cattle and other animals.

The trial results indicate the composition promotes rapid healing of surface abrasions and surgical wounds.

The applied compositions of Example 1 effectively acts as a true pseudoskin and as such allows rapid sub-membrane proliferation of an epithelial cellular layer. In this manner the contused surface is rapidly reepithelialised with associated minimisation of epithelial cellular hypertrophy and contracture.

Example 4

A Semipermeable Wound Spray, Example 1 Bandage for Dogs and Cats

The example 1 spray has been used in the treatment of wounds, dermatitis (eczema madidans), abscesses, furunculosis, otitis external and postoperative wounds. Before treatment with Example 1 composition, samples from the various conditions were taken for laboratory determination of bacteria.

Three days after treatment with Example 1 composition which formed a skin patch or bandage the treated area was evaluated for colour, sensibility, humidity and pus as well as water repellent quality, adhesiveness and scale production.

Ninety three animals, eighty dogs and thirteen cats, were treated with the Example 1 bandage.

The objective of the study was to ascertain:
1. Will it be possible for the Example 1 bandage to protect the wound and avoid water penetration.
2. Will the Example 1 bandage be able to stop the irritation and red erythema, characteristic of acute wounds and eczema madidans.

TABLE 3

Number of animals and age distribution in the test

| Diagnose | Number |
| --- | --- |
| Dermatitis | 13 |
| Flegmone, adsces | 7 |
| Furunculose | 4 |
| Operating | 55 |
| Otitis externa | 8 |
| Vulnus inc., morsum | 6 |

TABLE 4

The results of the bacteriological determination

| Cultivation results | Number |
| --- | --- |
| g+ and g– *Staphylococcus* | 21 |
| g-*Clostridium Staphylococcus* | 18 |
| *Haemolytic Staphylococcus* | 18 |
| *Proteus* | 2 |
| Anahaemolytic g-*Staphylococcus* | 3 |
| *Staphylococcus faecalis* | 1 |
| *Klebsiella* | 1 |

TABLE 4-continued

The results of the bacteriological determination

| Cultivation results | Number |
| --- | --- |
| Yeast g-*Staphylococcus* | 5 |
| Sterile after forty eight hours | 30 |

TABLE 5

The result of the clinical examination three days after treatment with Example 1 bandage.

| | Yes | No | % |
| --- | --- | --- | --- |
| Colour | 6 | 87 | 7 |
| Sensibility | 0 | 93 | 0 |
| Smell | 1 | 92 | 1 |
| Humidity | 22 | 71 | 24 |
| Pus | 5 | 88 | 5 |
| Water-repellent | 90 | 3 | 97 |
| Viscosity | 0 | 93 | 0 |
| Scate production | 3 | 90 | 3 |

CONCLUSION

The use of Example 1 bandage for minor cuts and wounds has shown that it relieves the erythema in 93% of the cases and that it has a water-repellent effect in 97%

From the results obtained Example 1 bandage obviously has a good antiseptic quality for treatment of minor cuts, post-operative wounds, dermatitis and abscesses.

Example 5

Spray On Antifungal Bandage for athlete foot caused by Tinea spp

Most common non-fatal skin infections are cause by various bacterial and fungi tinea pedis, tinea cruris, tinea corporis and cutancous candida albacan. Miconazole is one of the common antifungal agents against such infections. Miconazole appears to act on cell wall and membranes, inducing permeability changes that alter the ionic micromolecular composition of the affected cells. The recommended product strength containing miconazole (for example, Daktarin by Janssen—Cilag) is 2% as powder, tincture or cream applied twice daily to the infected area.

The difficulty of using an antibacterial/antifungal cream, tincture or powder for tinea infection is that the medication cannot adhere to the infected area. This is particularly true if the infection is on the foot (for example, athlete foot). This giving rises to unsatisfactory results and repeated infections.

The following example product formulation demonstrated the usefulness of the spray on patch delivery system, which greatly improves the efficacy of miconazole and the likes of antifungal agents. The formulation also contains Chlorbutanol, which is a traditional anti bacterial, and anti fungal agent the use of which is well documented in various pharmacopoeiae.

The spray on medicated patch adheres to surface of infected skin over a long period of time (about twenty four hours) delivering active ingredients continuously to the infected surface. In addition, the spray can be used to fungal proof footwear to prevent further re-infections. Product strength compared to other commercial product (for example, Daktarin) is halved (from 2% to 1%) and dosage rate is also halved to daily application only (from twice daily to once daily).

Spray On Antifungal Bandage for athlete foot caused by *Tinea* spp.

Formulae

| | | |
|---|---|---|
| Miconazole USP | 1.0% w/v | Active, antifungal |
| Chlorbutanol B/Eur. P | 0.6% w/v | Active, antibacterial/antifungal |
| Phenol BP/Eur. P | 0.2% w/v | Preservative |
| Poly methacrylate USNF | 10.0% w/v | Film former |
| Poly butyl Phthalate BP/Eur. P | 1.0% w/v | Film softener |
| Isopropanol USP | 24% w/v | Solvent |
| Acetone BP/Eur. P | 24% w/v | Solvent |
| Ethyl Acetate USP | 40.7% w/v | Solvent |
| Total | 100% w/v | |

Method of Manufacturing:

Dissolve miconazole and chlorbutanol in isopropanol, phenol, acetone and ethyl acetate. Add in Poly butyl phthalate. Add in Poly methacrylate with gentle stirring. Pack in spray apparatus.

Direction for Use:

The spray on medication adheres to skin effectively over twenty four hours. Spray on affected area to ensure adequate cover. Used as continues release antifungal spray once daily. To prevent reinfection, spray into foot ware daily during treatment and thereafter at least once weekly for six months.

A twenty five year old female used the above spray after repeatedly failed to eradicate the fugal problem on her right foot for over five years. Before application, the area was ulcerated, weeping and itchy The miconazole/chlorbutanol spray on bandage was used daily for five days. Her foot wear was fungal proofed by spraying the same product into the inside of the shoes once daily for five days. After five days, the infected area was visibly reduced. The use of the miconazole spray was stopped. After two weeks the area was clear of infections (no longer weeping, nor cracked, nor itchy and skin healed quite well). After the initial treatment, no incidence of reinfection was reported during the next six months.

A fifty five year old male also used the above spray for five days after failure to control severe fungal problem on the right foot for over ten years. Previous medications including iodine tincture, Daktarin cream, salicylic acid ointment and Nizoral cream.

The miconazole/chlorbutanol spray on patch was used daily for five days. The foot wear was fungal proofed by spraying the same product into the inside of the shoes once daily for five days. After five days, the infected area was visibly reduced. Skin lesions starts to heal there after. The use of the miconazole/chlorbutanol spray was continued for another five days and then stopped. After two weeks the area was clear of infections (no longer weeping, bleeding, cracked, or itchy). After the initial treatment, no incidence of reinfection was reported during the next six months. All footwear was fungal proof by spraying into footwear once weekly for about six months.

Example 6

Spray on Betamethasone bandage for allergic skin conditions, eczema and psoriasis Betamethasone is a corticosteroid indicated for treatment of allergic skin disorders. The product is marketed under the trade name of Betnovate™ as cream, ointment or gel containing betamethasone 0.05% to 0.1% strength. Dosage application is up to four times daily.

It is a well known practice in Australian hospitals that after applying the Betnovate™ cream, gel or ointment, efficacy can be improved by wrapping the area in "Glad Wrap"™ (a thin polymer film) to enhance absorption and prolong drug contact.

The following formulation is capable of replacing the "Glad Wrap" practice efficiently. Application is also reduced from up to four ties daily to once daily. Formulation also contains an effective antimicrobial agent that treat and prevents bacterial or fungal infections in case of weeping wound or ulcers.

Spray on Betamethasone bandage for allergic skin conditions, eczema and psoriasis

| | | |
|---|---|---|
| Betamethasone Valerate BP/Eur. P | 0.12% w/v | Active anti-inflammatory |
| Chlorbutanol BP/Eur. P | 0.6% w/v | Active antimicrobial agent |
| Triolosan (Ciba Geigy Irgasan DP300) | 0.1% w/v | Preservative |
| Poly methacrylate USNF | 10.0% w/v | Film former |
| Poly butyl Phthalate BP/Eur. P | 1.0% w/v | Film softener |
| Isopropanol USP | 24% w/v | Solvent |
| Acetone BP/Eur. P | 24% w/v | Solvent |
| Ethyl Acetate USP | 40.7% w/v | Solvent |
| Total | 100% w/v | |

Recommended Dosage:

Apply once daily to the affected area for treatment of eczema, psoriasis and allergic skin to conditions.

Method of Manufacture:

1. Dissolve betamethasone in the mixture of solvents. Add in Triclosan and Chlorbutanol.
2. Add Poly butyl phthalate then Poly methacrylate with gentle stirring.
3. Pack in airtight aluminum cans and attach actuator and spray nozzle.

Example of Use:

A twenty three year old female who suffers both eczema and psoriasis badly since birth has used Betnovate Cream on and off to relieve the skin irritation due to her condition. Her skin affliction was particularly bad during period of stress. She tried the formulated Betamethasone spray on bandage for two weeks prior to her university examination and found her condition is much improved. Symptomatic relieve was achieve within forty eight hours. Relieve of itch and weeping due to constant scratching was fast and effective. She only requires to use the spray once daily at night instead of morning and night She can wear the betamethsone spray bandage to shower without having to repeat application. The affected area heals well particularly where it is not practical to put a bandage on top to prevent clothes scratching on the affected area.

Example 7

Spray on Mepyramine Antihistamine Adhesive Patch—a first aid treatment for burns, scalds, insect bites, antipruritic and local analgesic application in all conditions characterized by intense itching or pain.

Mepyramine is a well known, well tried and well used antihistamine. Over a hundred medications contain mepyramine as one of its major ingredients.

| Spray on Mepyramine Antihistamine Adhesive Patch | | |
|---|---|---|
| Mepyramine Maleate BP/Eur. P | 2.0% w/v | Active antihistamine |
| Chlorbutanol BP/Eur. P | 0.6% w/v | Active antimicrobial agent |
| Triclosan (Ciba Geigy Irgasan DP300) | 0.1% w/v | Preservative |
| Poly methacrylate USNF | 10.0% w/v | Film former |
| Poly butyl Phthalate BP/Eur. P | 1.0% w/v | Film softener |
| Isopropanol USP | 24% w/v | Solvent |
| Acetone BP/Eur. P | 24% w/v | Solvent |
| Ethyl Acetate USP | 40.7% w/v | Solvent |
| Total | 100% w/v | |

Method of Manufacture;
1. Dissolve Mepyramine maleate in the mixture of solvents. Add in Triclosan and Chlorbutanol.
2. Add Poly butyl phthalate then Poly methacrylate with gentle stirring.
3. Pack in airtight aluminum cans and attach actuator and spray nozzle.

A group of boy scouts and parent used the Spray on Mepyramine Antihistamine Adhesive Patch during recent camping. General observation from adults indicated that the formulation relieved symptoms of insect bites fast and efficiently. In one occasion, a twelve year old boy scout was mildly burned by camp fire on the back of the hand while roasting marshmallow. After one application, pain was quickly relieved and no blister formed. It was indicated that the Mepyramine antihistmine spray on bandage also formed a protective cover for the would and was waterproof. The bandage remained on skin even after swimming and self disintegrated in about twenty-four hours.

Example 8

Further compositions are prepared as follows:
(A) Chlorhexidine acetate 0.5% w/w
   0.07% w/w of triclosane
   0.6% w/w of chlorbutanol
   10% w/w of polymethacrylic acid
   1.2% w/w of polybutylphthalate
   4% w/w of isopropanol
   24% w/w acetone
   ethylacetate up to 100% W/W
(B) Phenoxyethanol 2% w/w
   0.07% w/w of triclosane
   0.6% w/w of chlorbutanol
   10% w/w of polymethacrylic acid
   1.2% w/w of polybutylphthalate
   4% w/w of isopropanol
   24% w/w acetone
   ethylacetate up to 100% w/w
(C) Phenethyl alcohol 2%
   0.07% w/w of triclosane
   0.6% w/w of chlorbutanol
   10% W/W of polymethacrylic acid
   1.2% w/w of polybutylphthalate
   4% w/w of isopropanol
   24% w/w acetone
   ethylactate up to 100% w/w

The invention claimed is:
1. A non-aerosol sprayable skin patch composition consisting essentially of:
   (a) 0.01% to 10% w/w of at least one water-soluble physiologically active ingredient;
   (b) 1% to 50% w/w of at least one substantially water insoluble film forming agent selected from the group consisting of acrylic acid, polyacrylic acid, polybutylmethacrylate, polymethacrylic acid, ascorbyl palmitate, carbomer, cellulose acetate phthalate, hydroxyethyl cellulose, hydroxypropyl cellulose, hydroxypropyl methylcellulose, ethyl cellulose, hydroxypropyl methylcellulose phthalate, hypomellose phthalate, crospovidone, cetyl alcohol, poloaxmer, polyethylene glycol, polyvinyl acetate, polyvinyl acetate phthalate, polyvinyl alcohol, and povidone;
   (c) 0.1% to 20% w/w of at least one film plasticiser agent; and
   (d) 30% to 90% w/w of at least one volatile organic solvent,
wherein said composition forms a flexible, porous and physiologically compatible skin patch when sprayed onto skin and is allowed to dry, wherein said patch disintegrates progressively over a 24–48 hour time period.

2. The composition according to claim 1, wherein said at least one physiologically active ingredient is an antimicrobial agent and/or an antifungal agent.

3. The composition according to claim 2, wherein said antimicrobial agent is a quaternary ammonium compound.

4. The composition according to claim 3, wherein said quaternary ammonium compound is selected from the group consisting of cetrimide, alkylaryltrialkylammonium chloride, alkylaryltrimethylammonium chloride, amantanium bromide, benzalkonium chloride, benzethonium chloride, benzododecinium bromide, cetalkonium chloride, cethexonium bromide, centrimonium bromine, and cetyldimethylethylammonium bromide.

5. The composition according to claim 4, wherein said quaternary ammonium compound is cetrimide.

6. The composition according to claim 2, wherein said water-soluble compound is a mixture of a water-soluble antimicrobial agent and a water-soluble antifungal agent.

7. The compound according to claim 6, wherein said antimicrobial agent is a quaternary ammonium compound and said antifungal agent is selected from the group consisting of chlorbutanol, phenol, salicylic acids, arisoran, amoralfine, amphotericin, bifonazole, butoconazole nitrate, chlormidazole, clotrimazole, croconazole, econazole, enilconazole, fenticonazole, fluconazole, flutrimazole, isoconazole, itraconazole, ketoconazole, lanoconazole, miconazole, omoconazole, saperconazole, sertaconazole, sulconazole, terconazole, tioconazole, benzoyl disulphide, bromochlorosalicylanilide, buclosamide, butenafine, candicidicaprylic acid, chlorphenesin, ciclopirox olamine, cilofungin, fenticlor, flucytosine, criseofulvin, hachimycin, haloprogin, hamycin, hydroxystilbamidine, isethionate, loflucarban, mepartricin, natamycin, nifuroxime, p-nitrophenol, nystatin, pentamycin, propionic acid, protiofate, pyrrolnitrin, sulbentine, terbinafine, tolciclate, tolnaftate, triacetin, and undecenoic acid.

8. The compound according to claim 7, wherein said antifungal agent is chlorbutanol.

9. The composition according to claim 1, wherein said at least one physiologically active ingredient is selected from the group consisting of an antiseptic, an antiparasitic, a nicotine, a cortico steroid, a pain relieving agent, a cardiac dilater, a cardiac stimulant, an antihistamine, an anti-inflammatory, an anti blood clotting agent, a growth hormone, a sex hormone, a drug commonly used for diseases in the alimentary system, central nervous system, musculoskeletal system, genitourinary system allergy or immune system, and a biologically active peptide or protein.

10. The composition according to claim 9, wherein said at least one physiologically active ingredient is triclosan.

11. The composition according to claim 1, wherein the film forming agent is selected from the group consisting of polymethacrylic acid, polybutyl methacrylate and polyacrylic acid.

12. The composition according to claim 1, wherein said film plasticiser agent is polybutylphthalate.

13. The composition according to claim 1, wherein said organic solvent is selected from the group consisting of isopropanol, acetone and ethylacetate.

14. A non-aerosol sprayable skin patch composition consisting essentially of:
  (a) 0.01% to 10% w/w of at least one water-soluble physiologically active ingredient;
  (b) 1% to 50% w/w of polymethacrylic acid;
  (c) 0.1% to 20% w/w of polybutylphthalate;
  (d) 0% to 90% w/w of isopropanol;
  (e) 0% to 90% w/w of acetone; and
  (f) ethylacetate up to 100% w/w,
wherein said composition forms a flexible, porous and physiologically compatible skin patch when sprayed onto skin and is allowed to dry, and wherein said patch disintegrates progressively over a 24–48 hour time period.

15. The composition according to claim 14, consisting essentially of:
  (a) 0.05% w/w of cetrimide,
  (b) 0.07% w/w of triclosan,
  (c) 0.6% w/w of chlorbutanol,
  (d) 10% w/w of polymethacrylic acid,
  (e) 1.2% w/w of polybutylphthalate,
  (f) 4% w/w of isopropanol,
  (g) 24% w/w of acetone, and
  (h) ethylacetate up to 100% w/w.

16. A method of improving wound healing or administering a physiologically active ingredient to a patient comprising spraying on to a wound or on to skin of a patient in need thereof, an effective amount of a composition according to claim 1.

17. A method for the treatment of skin wounds, fungal infections, eczema, bacterial infections in or on the skin and/or associated with skin wounds, athlete's foot, skin ulceration, burns, scalds, insect bites, allergic skin diseases, psoriasis, itching and pain, which comprises spraying on to skin in need of such treatment a composition according to claim 1.

* * * * *